United States Patent
Cobb

(10) Patent No.: US 10,280,452 B2
(45) Date of Patent: May 7, 2019

(54) MUTATION ANALYSIS

(71) Applicant: Epistem Limited, Manchester (GB)

(72) Inventor: Ben Cobb, Manchester (GB)

(73) Assignee: Genedrive Diagnostics, Ltd., Manchester (GB)

( * ) Notice: Subject to any disclaimer, the term of this patent is extended or adjusted under 35 U.S.C. 154(b) by 0 days.

(21) Appl. No.: 15/026,296

(22) PCT Filed: Sep. 30, 2014

(86) PCT No.: PCT/GB2014/052939
§ 371 (c)(1),
(2) Date: Mar. 31, 2016

(87) PCT Pub. No.: WO2015/049496
PCT Pub. Date: Apr. 9, 2015

(65) Prior Publication Data
US 2016/0237481 A1 Aug. 18, 2016

(30) Foreign Application Priority Data

Oct. 1, 2013 (GB) .................................. 1317355.4

(51) Int. Cl.
*C12Q 1/68* (2018.01)
*C07H 21/00* (2006.01)
*C12Q 1/6827* (2018.01)
*C12Q 1/6858* (2018.01)
*C12Q 1/6806* (2018.01)

(52) U.S. Cl.
CPC ......... *C12Q 1/6827* (2013.01); *C12Q 1/6806* (2013.01); *C12Q 1/6858* (2013.01)

(58) Field of Classification Search
CPC .................................. C07H 21/00; C12Q 1/68
See application file for complete search history.

(56) References Cited

U.S. PATENT DOCUMENTS

| 9,005,932 B2* | 4/2015 | Cobb | C12Q 1/6858 |
|---|---|---|---|
| | | | 435/6.1 |
| 2002/0051986 A1* | 5/2002 | Baez | C12Q 1/6804 |
| | | | 435/6.11 |
| 2005/0118623 A1* | 6/2005 | Belousov | C12Q 1/6827 |
| | | | 435/6.14 |
| 2006/0263857 A1* | 11/2006 | Lefrancois | C07K 14/5443 |
| | | | 435/69.52 |
| 2008/0096766 A1* | 4/2008 | Lee | C12Q 1/6851 |
| | | | 506/6 |
| 2008/0305478 A1* | 12/2008 | Chun | C12Q 1/6848 |
| | | | 435/6.11 |
| 2010/0055798 A1 | 3/2010 | Battersby | |
| 2014/0206564 A1* | 7/2014 | Rice | C12Q 1/701 |
| | | | 506/9 |

FOREIGN PATENT DOCUMENTS

| WO | WO-2005/035545 A2 | 4/2005 |
| WO | WO-2009/090311 A2 | 7/2009 |
| WO | WO-2012/093262 A2 | 7/2012 |
| WO | WO-2013/041853 A1 | 3/2013 |

OTHER PUBLICATIONS

Hirano et al., J. of Clinical Microbiology 37(8) : 2663 (1999).*
Hwang et al., Biotechniques 35(6) :1180 (2003). Provided in copending U.S. Appl. No. 14/345,829.*
Howell et al. Nature Biotechnology 17 : 87-88(1999).*
French, D. et al., Analysis of multiple single nucleotide polymorphisms closely positioned in the ovine PRNP gene using linear fluorescent probes and melting curve analysis, BMC Infectious Diseases, 7(90):10 pages (2007).
International Search Report for PCT/GB2014/052939, 6 pages (dated Feb. 3, 2015).
Written Opinion for PCT/GB2014/052939, 7 pages (dated Feb. 3, 2015).
Yu, X. et al., Development and Validation of a Diagnostic DNA Microarray to Detect Quinolone-Resistant *Escherichia coli* among Clinical Isolates, Journal of Clinical Microbiology, 42(9):4083-4091 (2004).

* cited by examiner

*Primary Examiner* — Ethan C Whisenant
(74) *Attorney, Agent, or Firm* — Choate, Hall & Stewart, LLP; Brenda Herschbach Jarrell; Michael L. Vetter

(57) ABSTRACT

A method and an oligonucleotide probe are described for determining the presence or absence of mutant alleles in a genomic locus. The probe binds to different alleles of a target sequence with different melting temperatures (Tm). The method determines the Tm of the probe when it is hybridized to the target sequence to establish whether a variant nucleic acid such as a mutant allele is present or absent in the target sequence. There may be variants in a target sequence that are not of interest, for example phenotypically silent mutations. To ensure that these variants do not influence the Tm of the probe, the probe contains universal base sites where such variants of no interest occur.

17 Claims, 9 Drawing Sheets
Specification includes a Sequence Listing.

Fig.5 rpoB (507>520) Linked-Probe

(5'>3')
3GGGTTG1TCTGG1CCATGAATTGGCT*****CAGC1GGCTGG1GCCGAAGAA2 rpoB (507>520)

(5'>3')
GGGTTG1TCTGG1CCATGAATTGGCTCAGCTGGCTGGTGCCGAAGAA rpoB (520>533) Linked-Probe

(5'>3')
3CAGCGCCGACAG1CGGCG*****CT1GTGG1CAACCCCGACAGC2 rpoB (520>533)

CAGCGCCGACAGTCGGCGCT1GTGG1CAACCCCGACAGC rpoB (507>520) silent 1

(5'>3')
3GGGTTG1TCTGG1CCAT4AATTGGCT*****CAGC1GGCTGG4GCCGAAGAA2 rpoB (507>520) short

3GGGTTG1TCTGG1CCAT*****AATTGGCTCAGC1GGCTGG4GCC2 rpoB (520>533) silence all

(5'>3')
34AG4GC4GA4AG1CG4CG*****CT1GTG4C1CAA4CC4GA4AGC2 rpoB (507>520) silence all

(5'>3')
3GGGTTG1TCTGG1CCAT4AATTGGCT*****4AGC1GGCT4GT4CCGAAGAA2 rpoB (507>520) shortA

3GGGTTG[1]TCTGG[1]CCATG*****AATTGGCTCAGC[1]GGCTGGT[4]CC2 rpoB (507>520) shortB (5'>3')

3GGGTTG[1]TCTGG[1]CCATG*****AATTGGCT[4]AGC[1]GGCT[4]GT[4]CC2

1 = fluorescein dT
2 = phosphate block
3 = TRIMETHOXYSTILBENE
4 = 5-nitroindole
* = Inosine residues (5 per probe)

Fig.9
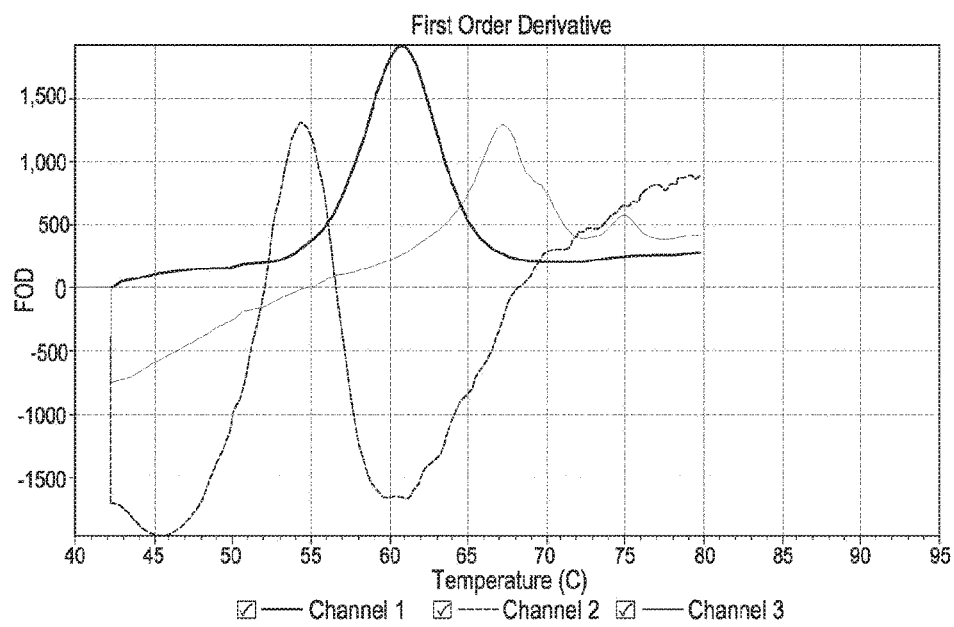
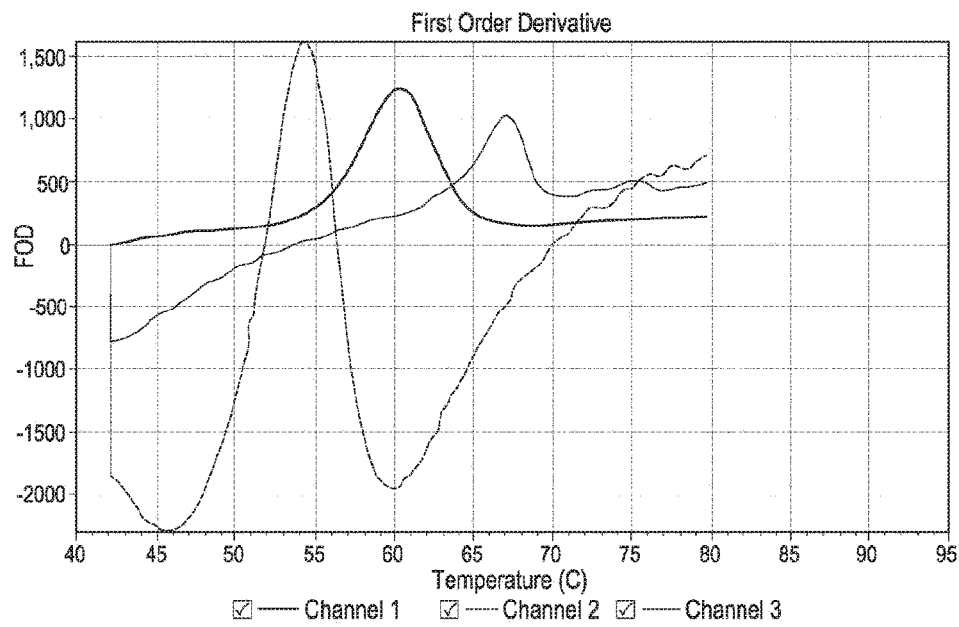

SEQUENCE LISTING

<160> NUMBER OF SEQ ID NOS: 80

<210> SEQ ID NO 1
<211> LENGTH: 52
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' trimethoxystilbene
<220> FEATURE:
<221> NAME/KEY: modified_base
<222> LOCATION: (7)..(7)
<223> OTHER INFORMATION: Fluorescein dT
<220> FEATURE:
<221> NAME/KEY: modified_base
<222> LOCATION: (13)..(13)
<223> OTHER INFORMATION: Fluorescein dT
<220> FEATURE:
<221> NAME/KEY: modified_base
<222> LOCATION: (18)..(18)
<223> OTHER INFORMATION: 5-nitroindole
<220> FEATURE:
<221> NAME/KEY: modified_base
<222> LOCATION: (27)..(31)
<223> OTHER INFORMATION: Inosine
<220> FEATURE:
<221> NAME/KEY: modified_base
<222> LOCATION: (36)..(36)
<223> OTHER INFORMATION: Fluorescein dT
<220> FEATURE:
<221> NAME/KEY: modified_base
<222> LOCATION: (43)..(43)
<223> OTHER INFORMATION: 5-nitroindole
<220> FEATURE:
<223> OTHER INFORMATION: 3' phosphate block

<400> SEQUENCE: 1
gggttgttct ggtccatnaa ttggctnnnn ncagctggct ggngccgaag aa    52

<210> SEQ ID NO 2
<211> LENGTH: 45
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' trimethoxystilbene
<220> FEATURE:
<221> NAME/KEY: modified_base
<222> LOCATION: (7)..(7)
<223> OTHER INFORMATION: Fluorescein dT
<220> FEATURE:
<221> NAME/KEY: modified_base
<222> LOCATION: (13)..(13)
<223> OTHER INFORMATION: Fluorescein dT
<220> FEATURE:
<221> NAME/KEY: modified_base
<222> LOCATION: (18)..(22)
<223> OTHER INFORMATION: Inosine
<220> FEATURE:
<221> NAME/KEY: modified_base
<222> LOCATION: (35)..(35)
<223> OTHER INFORMATION: Fluorescein dT
<220> FEATURE:
<221> NAME/KEY: modified_base
<222> LOCATION: (42)..(42)
<223> OTHER INFORMATION: 5-nitroindole
<220> FEATURE:
<223> OTHER INFORMATION: 3' phosphate block

<400> SEQUENCE: 2
gggttgttct ggtccatnnn nnaattggct cagctggctg gngcc    45

```
<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence: Synthetic
      probe
<220> FEATURE
<223> OTHER INFORMATION: 5' trimethoxystilbene
<220> FEATURE:
<221> NAME/KEY: modified_base
<222> LOCATION: (1)..(1)
<223> OTHER INFORMATION: 5-nitroindole
<220> FEATURE:
<221> NAME/KEY: modified_base
<222> LOCATION: (4)..(4)
<223> OTHER INFORMATION: 5-nitroindole
<220> FEATURE:
<221> NAME/KEY: modified_base
<222> LOCATION: (7)..(7)
<223> OTHER INFORMATION: 5-nitroindole
<220> FEATURE:
<221> NAME/KEY: modified_base
<222> LOCATION: (10)..(10)
<223> OTHER INFORMATION: 5-nitroindole
<220> FEATURE:
<221> NAME/KEY: modified_base
<222> LOCATION: (13)..(13)
<223> OTHER INFORMATION: Fluorescein dT
<220> FEATURE:
<221> NAME/KEY: modified_base
<222> LOCATION: (16)..(16)
<223> OTHER INFORMATION: 5-nitroindole
<220> FEATURE:
<221> NAME/KEY: modified_base
<222> LOCATION: (19)..(23)
<223> OTHER INFORMATION: Inosine
<220> FEATURE:
<221> NAME/KEY: modified_base
<222> LOCATION: (26)..(26)
<223> OTHER INFORMATION: Fluorescein dT
<220> FEATURE:
<221> NAME/KEY: modified_base
<222> LOCATION: (30)..(30)
<223> OTHER INFORMATION: 5-nitroindole
<220> FEATURE:
<221> NAME/KEY: modified_base
<222> LOCATION: (32)..(32)
<223> OTHER INFORMATION: Fluorescein dT
<220> FEATURE:
<221> NAME/KEY: modified_base
<222> LOCATION: (36)..(36)
<223> OTHER INFORMATION: 5-nitroindole
<220> FEATURE:
<221> NAME/KEY: modified_base
<222> LOCATION: (39)..(39)
<223> OTHER INFORMATION: 5-nitroindole
<220> FEATURE:
<221> NAME/KEY: modified_base
<222> LOCATION: (42)..(42)
<223> OTHER INFORMATION: 5-nitroindole
<220> FEATURE:
<223> OTHER INFORMATION: 3' phosphate block

<400> SEQUENCE: 3
nagngcngan agtcgncgnn nnncttgtgn gtcaanccng anagc            45

<210> SEQ ID NO 4
<211> LENGTH: 52
<212> TYPE: DNA
<213> ORGANISM: Artificial Sequence
<220> FEATURE:
<223> OTHER INFORMATION: Description of Artificial Sequence: Synthetic
      probe
<220> FEATURE:
```

```
<223> OTHER INFORMATION: 5' trimethoxystilbene
<220> FEATURE:
<221> NAME/KEY: modified_base
<222> LOCATION: (7)..(7)
<223> OTHER INFORMATION: Fluorescein dT
<220> FEATURE:
<221> NAME/KEY: modified_base
<222> LOCATION: (13)..(13)
<223> OTHER INFORMATION: Fluorescein dT
<220> FEATURE:
<221> NAME/KEY: modified_base
<222> LOCATION: (18)..(18)
<223> OTHER INFORMATION: 5-nitroindole
<220> FEATURE:
<221> NAME/KEY: modified_base
<222> LOCATION: (27)..(31)
<223> OTHER INFORMATION: Inosine
<220> FEATURE:
<221> NAME/KEY: modified_base
<222> LOCATION: (32)..(32)
<223> OTHER INFORMATION: 5-nitroindole
<220> FEATURE:
<221> NAME/KEY: modified_base
<222> LOCATION: (36)..(36)
<223> OTHER INFORMATION: Fluorescein dT
<220> FEATURE:
<221> NAME/KEY: modified_base
<222> LOCATION: (41)..(41)
<223> OTHER INFORMATION: 5-nitroindole
<220> FEATURE:
<221> NAME/KEY: modified_base
<222> LOCATION: (44)..(44)
<223> OTHER INFORMATION: 5-nitroindole
<220> FEATURE:
<223> OTHER INFORMATION: 3' phosphate block

<400> SEQUENCE: 4
gggttgttct ggtccatnaa ttggctnnnn nnagctggct ngtnccgaag aa             52

<210> SEQ ID NO 5
<211> LENGTH: 46
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' trimethoxystilbene
<220> FEATURE:
<221> NAME/KEY: modified_base
<222> LOCATION: (7)..(7)
<223> OTHER INFORMATION: Fluorescein dT
<220> FEATURE:
<221> NAME/KEY: modified_base
<222> LOCATION: (13)..(13)
<223> OTHER INFORMATION: Fluorescein dT
<220> FEATURE:
<221> NAME/KEY: modified_base
<222> LOCATION: (19)..(23)
<223> OTHER INFORMATION: Inosine
<220> FEATURE:
<221> NAME/KEY: modified_base
<222> LOCATION: (36)..(36)
<223> OTHER INFORMATION: Fluorescein dT
<220> FEATURE:
<221> NAME/KEY: modified_base
<222> LOCATION: (44)..(44)
<223> OTHER INFORMATION: 5-nitroindole
<220> FEATURE:
<223> OTHER INFORMATION: 3' phosphate block

<400> SEQUENCE: 5
gggttgttct ggtccatgnn nnnaattggc tcagctggct ggtncc                   46

<210> SEQ ID NO 6
```

<211> LENGTH: 46
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' trimethoxystilbene
<220> FEATURE:
<221> NAME/KEY: modified_base
<222> LOCATION: (7)..(7)
<223> OTHER INFORMATION: Fluorescein dT
<220> FEATURE:
<221> NAME/KEY: modified_base
<222> LOCATION: (13)..(13)
<223> OTHER INFORMATION: Fluorescein dT
<220> FEATURE:
<221> NAME/KEY: modified_base
<222> LOCATION: (19)..(23)
<223> OTHER INFORMATION: Inosine
<220> FEATURE:
<221> NAME/KEY: modified_base
<222> LOCATION: (32)..(32)
<223> OTHER INFORMATION: 5-nitroindole
<220> FEATURE:
<221> NAME/KEY: modified_base
<222> LOCATION: (36)..(36)
<223> OTHER INFORMATION: Fluorescein dT
<220> FEATURE:
<221> NAME/KEY: modified_base
<222> LOCATION: (41)..(41)
<223> OTHER INFORMATION: 5-nitroindole
<220> FEATURE:
<221> NAME/KEY: modified_base
<222> LOCATION: (44)..(44)
<223> OTHER INFORMATION: 5-nitroindole
<220> FEATURE:
<223> OTHER INFORMATION: 3' phosphate block

<400> SEQUENCE: 6
gggttgttct ggtccatgnn nnnaattggc tnagctggct ngtncc                46

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' trimethoxystilbene
<220> FEATURE:
<221> NAME/KEY: modified_base
<222> LOCATION: (1)..(1)
<223> OTHER INFORMATION: 5-nitroindole
<220> FEATURE:
<221> NAME/KEY: modified_base
<222> LOCATION: (4)..(4)
<223> OTHER INFORMATION: 5-nitroindole
<220> FEATURE:
<221> NAME/KEY: modified_base
<222> LOCATION: (7)..(7)
<223> OTHER INFORMATION: 5-nitroindole
<220> FEATURE:
<221> NAME/KEY: modified_base
<222> LOCATION: (10)..(10)
<223> OTHER INFORMATION: 5-nitroindole
<220> FEATURE:
<221> NAME/KEY: modified_base
<222> LOCATION: (13)..(13)
<223> OTHER INFORMATION: Fluorescein dT
<220> FEATURE:
<221> NAME/KEY: modified_base
<222> LOCATION: (16)..(16)
<223> OTHER INFORMATION: 5-nitroindole
<220> FEATURE:
<221> NAME/KEY: modified_base

```
<222> LOCATION: (19)..(23)
<223> OTHER INFORMATION: Inosine
<220> FEATURE:
<221> NAME/KEY: modified_base
<222> LOCATION: (26)..(26)
<223> OTHER INFORMATION: Fluorescein dT
<220> FEATURE:
<221> NAME/KEY: modified_base
<222> LOCATION: (30)..(30)
<223> OTHER INFORMATION: 5-nitroindole
<220> FEATURE:
<221> NAME/KEY: modified_base
<222> LOCATION: (32)..(32)
<223> OTHER INFORMATION: Fluorescein dT
<220> FEATURE:
<221> NAME/KEY: modified_base
<222> LOCATION: (36)..(36)
<223> OTHER INFORMATION: 5-nitroindole
<220> FEATURE:
<221> NAME/KEY: modified_base
<222> LOCATION: (39)..(39)
<223> OTHER INFORMATION: 5-nitroindole
<220> FEATURE:
<221> NAME/KEY: modified_base
<222> LOCATION: (42)..(42)
<223> OTHER INFORMATION: 5-nitroindole
<220> FEATURE:
<223> OTHER INFORMATION: 3' phosphate block

<400> SEQUENCE: 7
nagngcngan agncgncgnn nnnctngtgn gncaanccng anagc               45

<210> SEQ ID NO 8
<211> LENGTH: 52
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' trimethoxystilbene
<220> FEATURE:
<221> NAME/KEY: modified_base
<222> LOCATION: (7)..(7)
<223> OTHER INFORMATION: Fluorescein dT
<220> FEATURE:
<221> NAME/KEY: modified_base
<222> LOCATION: (13)..(13)
<223> OTHER INFORMATION: Fluorescein dT
<220> FEATURE:
<221> NAME/KEY: modified_base
<222> LOCATION: (18)..(18)
<223> OTHER INFORMATION: 5-nitroindole
<220> FEATURE:
<221> NAME/KEY: modified_base
<222> LOCATION: (27)..(31)
<223> OTHER INFORMATION: Inosine
<220> FEATURE:
<221> NAME/KEY: modified_base
<222> LOCATION: (32)..(32)
<223> OTHER INFORMATION: 5-nitroindole
<220> FEATURE:
<221> NAME/KEY: modified_base
<222> LOCATION: (36)..(36)
<223> OTHER INFORMATION: Fluorescein dT
<220> FEATURE:
<221> NAME/KEY: modified_base
<222> LOCATION: (41)..(41)
<223> OTHER INFORMATION: 5-nitroindole
<220> FEATURE:
<221> NAME/KEY: modified_base
<222> LOCATION: (44)..(44)
<223> OTHER INFORMATION: 5-nitroindole
<220> FEATURE:
<223> OTHER INFORMATION: 3' phosphate block

<400> SEQUENCE: 8
```
gggttgntct ggnccatnaa ttggctnnnn nnagcnggct ngtnccgaag aa     52

<210> SEQ ID NO 9
<211> LENGTH: 46
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' trimethoxystilbene
<220> FEATURE:
<221> NAME/KEY: modified_base
<222> LOCATION: (7)..(7)
<223> OTHER INFORMATION: Fluorescein dT
<220> FEATURE:
<221> NAME/KEY: modified_base
<222> LOCATION: (13)..(13)
<223> OTHER INFORMATION: Fluorescein dT
<220> FEATURE:
<221> NAME/KEY: modified_base
<222> LOCATION: (19)..(23)
<223> OTHER INFORMATION: Inosine
<220> FEATURE:
<221> NAME/KEY: modified_base
<222> LOCATION: (36)..(36)
<223> OTHER INFORMATION: Fluorescein dT
<220> FEATURE:
<221> NAME/KEY: modified_base
<222> LOCATION: (44)..(44)
<223> OTHER INFORMATION: 5-nitroindole
<220> FEATURE:
<223> OTHER INFORMATION: 3' phosphate block

<400> SEQUENCE: 9
gggttgntct ggnccatgnn nnnaattggc tcagcnggct ggtncc     46

<210> SEQ ID NO 10
<211> LENGTH: 46
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' trimethoxystilbene
<220> FEATURE:
<221> NAME/KEY: modified_base
<222> LOCATION: (7)..(7)
<223> OTHER INFORMATION: Fluorescein dT
<220> FEATURE:
<221> NAME/KEY: modified_base
<222> LOCATION: (13)..(13)
<223> OTHER INFORMATION: Fluorescein dT
<220> FEATURE:
<221> NAME/KEY: modified_base
<222> LOCATION: (19)..(23)
<223> OTHER INFORMATION: Inosine
<220> FEATURE:
<221> NAME/KEY: modified_base
<222> LOCATION: (32)..(32)
<223> OTHER INFORMATION: 5-nitroindole
<220> FEATURE:
<221> NAME/KEY: modified_base
<222> LOCATION: (36)..(36)
<223> OTHER INFORMATION: Fluorescein dT
<220> FEATURE:
<221> NAME/KEY: modified_base
<222> LOCATION: (41)..(41)
<223> OTHER INFORMATION: 5-nitroindole
<220> FEATURE:
<221> NAME/KEY: modified_base
<222> LOCATION: (44)..(44)
<223> OTHER INFORMATION: 5-nitroindole
<220> FEATURE:

<223> OTHER INFORMATION: 3' phosphate block

<400> SEQUENCE: 10
gggttgntct ggnccatgnn nnnaattggc tnagcnggct ngtncc                          46

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcagacgttg atcaacatcc                                                      20

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cgtggaggcg atcacaccgc agacgtt                                              27

<210> SEQ ID NO 13
<211> LENGTH: 52
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' trimethoxystilbene
<220> FEATURE:
<221> NAME/KEY: modified_base
<222> LOCATION: (7)..(7)
<223> OTHER INFORMATION: Fluorescein dT
<220> FEATURE:
<221> NAME/KEY: modified_base
<222> LOCATION: (13)..(13)
<223> OTHER INFORMATION: Fluorescein dT
<220> FEATURE:
<221> NAME/KEY: modified_base
<222> LOCATION: (27)..(31)
<223> OTHER INFORMATION: Inosine
<220> FEATURE:
<221> NAME/KEY: modified_base
<222> LOCATION: (36)..(36)
<223> OTHER INFORMATION: Fluorescein dT
<220> FEATURE:
<221> NAME/KEY: modified_base
<222> LOCATION: (43)..(43)
<223> OTHER INFORMATION: Fluorescein dT
<220> FEATURE:
<223> OTHER INFORMATION: 3' phosphate block

<400> SEQUENCE: 13
gggttgttct ggtccatgaa ttggctnnnn ncagctggct ggtgccgaag aa                  52

<210> SEQ ID NO 14
<211> LENGTH: 47
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base

```
<222> LOCATION: (7)..(7)
<223> OTHER INFORMATION: Fluorescein dT
<220> FEATURE:
<221> NAME/KEY: modified_base
<222> LOCATION: (13)..(13)
<223> OTHER INFORMATION: Fluorescein dT

<400> SEQUENCE: 14
gggttgttct ggtccatgaa ttggctcagc tggctggtgc cgaagaa        47

<210> SEQ ID NO 15
<211> LENGTH: 45
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' trimethoxystilbene
<220> FEATURE:
<221> NAME/KEY: modified_base
<222> LOCATION: (13)..(13)
<223> OTHER INFORMATION: Fluorescein dT
<220> FEATURE:
<221> NAME/KEY: modified_base
<222> LOCATION: (19)..(23)
<223> OTHER INFORMATION: Inosine
<220> FEATURE:
<221> NAME/KEY: modified_base
<222> LOCATION: (26)..(26)
<223> OTHER INFORMATION: Fluorescein dT
<220> FEATURE:
<221> NAME/KEY: modified_base
<222> LOCATION: (32)..(32)
<223> OTHER INFORMATION: Fluorescein dT
<220> FEATURE:
<223> OTHER INFORMATION: 3' phosphate block

<400> SEQUENCE: 15
cagcgccgac agtcggcgnn nnncttgtgg gtcaaccccg acagc         45

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (21)..(21)
<223> OTHER INFORMATION: Fluorescein dT
<220> FEATURE:
<221> NAME/KEY: modified_base
<222> LOCATION: (27)..(27)
<223> OTHER INFORMATION: Fluorescein dT

<400> SEQUENCE: 16
cagcgccgac agtcggcgct tgtgggtcaa ccccgacagc              40

<210> SEQ ID NO 17
<211> LENGTH: 87
<212> TYPE: DNA
<213> ORGANISM: Mycobacterium tuberculosis

<400> SEQUENCE: 17
ttcttcggca ccagccagct gagccaattc atggaccaga acaacccgct gtcggggttg    60
acccacaagc gccgactgtc ggcgctg                                         87

<210> SEQ ID NO 18
```

```
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ttcttcggtc acagccagct gagccaattc atggaccaga acaacccgct gtcggcgttg      60
acccgcaagc gccgactgtc ggcgctg                                         87

<210> SEQ ID NO 19
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ttcttcgata ccagccagct gagctaattc atggaccaga acaacccgct gtcggggttg      60
acctacaagc gccgactgtc cgcgctg                                         87

<210> SEQ ID NO 20
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ttcttcagcc ccagccagct gagccaattc atggaccaga acaacccgct gtcggggttg      60
acccacaagc gccgactgtc ggcgctg                                         87

<210> SEQ ID NO 21
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ttcttcggta ccagccagct gagccaattc atggaccaga acaacccgct gtcggcgttg      60
acccacaagc gccgactgtc ggcgctg                                         87

<210> SEQ ID NO 22
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ttcttcgata ccagccagct gagccaattc atggaccaga acaacccgct gtcggggttg      60
acccacaagc gccgactgtc ggcgctg                                         87

<210> SEQ ID NO 23
<211> LENGTH: 87
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 23
ttcttcggta ccagccagct gagccaattc atggaccaga acaacccgct gtcggggttg      60
acccacaagc gccgactgtc ggcgctg                                         87

<210> SEQ ID NO 24
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ttcttcagca ccagccagct gagccaattc atggaccaga acaacccgct gtcggggttg      60
acccacaagc gccgactgtc ggcgctg                                         87

<210> SEQ ID NO 25
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ttcttcggcc ccagccagct gagccaattc atgcaccaga acaacccgct gtcggggttg      60
acccgcaagc gccgactgtc ggcgctg                                         87

<210> SEQ ID NO 26
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ttcttcggcg ccagccagct gagccaattc atggaccaga acaacccgct gtcggcgttg      60
acccacaagc gccgactgtc ggcgctg                                         87

<210> SEQ ID NO 27
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ttcttcggcg ccagccagct gagccaattc atggaccaga acaacccgct gtcggggttg      60
acccacaagc gccgactgtc ggcgctg                                         87

<210> SEQ ID NO 28
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
```
ttcttcggcc acagccagct gagccaattc atggaccaga acaacccgct gtcggggttg    60
acccacaagc gccgactgtc ggcgctg    87

<210> SEQ ID NO 29
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ttcttcggcc ccagccagct gagccaattc atggaccaga acaacccgct gtcggggttg    60
acccacaagc gccgactgtc ggcgctg    87

<210> SEQ ID NO 30
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ttcttcggca ccagccaggt gagcgaattc atggaccaga acaagccgct gtcggggttg    60
acccgcaagc gccgactgtc ggcgctg    87

<210> SEQ ID NO 31
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ttcttcggca ccagccagcc gagccaattc atggaccaga acaacccgct gtcggcgttg    60
acccacaagc gccgactgtc ggcgctg    87

<210> SEQ ID NO 32
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ttcttcggca ccagccagcg cagccaattc atggaccaga acaacccgct gtcggggttg    60
acccacaagc gccgactgtc ggcgctg    87

<210> SEQ ID NO 33
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ttcttcggca ccagccagcc gagccaattc atggaccaga acaacccgct gtcggggttg    60
acccacaagc gccgactgtc ggcgctg    87

<210> SEQ ID NO 34
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ttcttcggca ccagccaggt gagccaattc atggaccaga acaacccgct gtcggggttg       60
acccacaagc gccgactgtc ggcgctg                                          87

<210> SEQ ID NO 35
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ttcttcggca ccagccagct gggcaatttc atggaccaga acaacccgct gtcggggttg       60
accttcaagc gccgactgtt ggcgctg                                          87

<210> SEQ ID NO 36
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ttcttcggca ccagccagct gggccaattc atggaccaga acaacccgct gtcggggttg       60
acccacaagc gccgactgtc ggcgctg                                          87

<210> SEQ ID NO 37
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ttcttcggca ccagccagct gagcaatttc atggaccaga acaacccgct gtcggggttg       60
acccacaagc gccgactgtc ggcgctg                                          87

<210> SEQ ID NO 38
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ttcttcggca ccagccagct gagcgaattc atggaccaga acaacccgct gtcggggttg       60
acccacaagc gccgactgtc ggcgctg                                          87

<210> SEQ ID NO 39
<211> LENGTH: 87

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ttcttcggca ccagccagct gagccacttc atggaccaga acaacccgct gtcggggttg      60
acccacaagc gccgactgtc ggcgctg                                          87

<210> SEQ ID NO 40
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ttcttcggca ccagccagct gagcccattc atggaccaga acaacccgct gtcggggttg      60
acccacaagc gccgactgtc ggcgctg                                          87

<210> SEQ ID NO 41
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ttcttcggca ccagccagct gagctaattc atggaccaga acaacccgct gtcggggttg      60
acccacaagc gccgactgtc ggcgctg                                          87

<210> SEQ ID NO 42
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ttcttcggca ccagccagct gagccaaatg gaccagaaca cccgctgtc ggggttgacc       60 cacaagcgcc gactgtcggc gctg                                             84

<210> SEQ ID NO 43
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ttcttcggca ccagccagct gagccaattt atggaccaga acaacccgct gtcggggttg      60
acccacaagc gccgactgtc ggcgctg                                          87

<210> SEQ ID NO 44
<211> LENGTH: 87
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 44
ttcttcggca ccagccagct gagccaagtc atggaccaga caacccgct gtcggggttg    60 acccacaagc gccgactgtc ggcgctg    87

<210> SEQ ID NO 45
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ttcttcggca ccagccagct gagccaattc gaccagaaca cccgctgtc ggggttgacc    60 cacaagcgcc gactgtcggc gctg    84

<210> SEQ ID NO 46
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ttcttcggca ccagccagct gagccaattc atagaccaga caacccgct gtcggggttg    60 acccacaagc gccgactgtc ggcgctg    87

<210> SEQ ID NO 47
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ttcttcggca ccagccagct gagccaattc atgcagaaca cccgctgtc ggggttgacc    60 cacaagcgcc gactgtcggc gctg    84

<210> SEQ ID NO 48
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ttcttcggca ccagccagct gagccaattc atggagcaga caacccgct gtcggggttg    60 acccacaagc gccgactgtc ggcgctg    87

<210> SEQ ID NO 49
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49

```
ttcttcggca ccagccagct gagccaattc atgggccaga caacccgct gtcggggttg      60 acccacaagc gccgactgtc ggcgctg                                         87
```

<210> SEQ ID NO 50
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50

```
ttcttcggca ccagccagct gagccaattc atgcaccaga caacccgct gtcggggttg      60 acccacaagc gccgactgtc ggcgctg                                         87
```

<210> SEQ ID NO 51
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51

```
ttcttcggca ccagccagct gagccaattc atgtaccaga caacccgct gtcggggttg      60 acccacaagc gccgactgtc ggcgctg                                         87
```

<210> SEQ ID NO 52
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52

```
ttcttcggca ccagccagct gagccaattc atggtccaga caacccgct gtcggggttg      60 acccacaagc gccgactgtc ggcgctg                                         87
```

<210> SEQ ID NO 53
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53

```
ttcttcggca ccagccagct gagccaattc atggacaaca acccgctgtc ggggttgacc    60
cacaagcgcc gactgtcggc gctg                                            84
```

<210> SEQ ID NO 54
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54

```
ttcttcggca ccagccagct gagccaattc atggaccaga acccgctgtc ggggttgacc    60
cacaagcgcc gactgtcggc gctg                                            84
```

<210> SEQ ID NO 55
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ttcttcggca ccagccagct gagccaattc atggaccagc acaacccgct gtcggggttg      60
acccacaagc gccgactgtc ggcgctg                                          87

<210> SEQ ID NO 56
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ttcttcggca ccagccagct gagccaattc atggaccaga acaagccgct gtcggggttg      60
acccacaagc gccgactgtc ggcgctg                                          87

<210> SEQ ID NO 57
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ttcttcggca ccagccagct gagccaattc atggaccaga acaacccgct gttggggttg      60
acccacaagc gccgactgtc ggcgctg                                          87

<210> SEQ ID NO 58
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ttcttcggca ccagccagct gagccaattc atggaccaga acaacccgct gtcggcgttg      60
accaacaagc gccgactgtc ggcgctg                                          87

<210> SEQ ID NO 59
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ttcttcggca ccagccagct gagccaattc atggaccaga acaacccgct gtcggcgttg      60
acccacaagc gccgactgtt ggcgctg                                          87

<210> SEQ ID NO 60
<211> LENGTH: 87
<212> TYPE: DNA

<213> ORGANISM: Artificial Sequence
<220> FEATURE:
<223> OTHER INFORMATION: Description of Artificial Sequence: Synthetic oligonucleotide

<400> SEQUENCE: 60
ttcttcggca ccagccagct gagccaattc atggaccaga acaacccgct gtcggcgttg     60
acccacaagc gccgactgtc ggcgctg                                        87

<210> SEQ ID NO 61
<211> LENGTH: 87
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 61
ttcttcggca ccagccagct gagccaattc atggaccaga acaacccgct gtcggggtgg     60
acccacaagc gccgactgtc ggcgctg                                        87

<210> SEQ ID NO 62
<211> LENGTH: 87
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 62
ttcttcggca ccagccagct gagccaattc atggaccaga acaacccgct gtcggggttg     60
ccccacaagc gccgactgtc ggcgctg                                        87

<210> SEQ ID NO 63
<211> LENGTH: 87
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 63
ttcttcggca ccagccagct gagccaattc atggaccaga acaacccgct gtcggggttg     60
acctacaagc gccgactgtc ggcgctg                                        87

<210> SEQ ID NO 64
<211> LENGTH: 87
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 64
ttcttcggca ccagccagct gagccaattc atggaccaga acaacccgct gtcggggttg     60
accaacaagc gccgactgtc ggcgctg                                        87

<210> SEQ ID NO 65
<211> LENGTH: 87
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 65
ttcttcggca ccagccagct gagccaattc atggaccaga acaacccgct gtcggggttg    60
accgacaagc gccgactgtc ggcgctg                                        87

<210> SEQ ID NO 66
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
ttcttcggca ccagccagct gagccaattc atggaccaga acaacccgct gtcggggttg    60
accttcaagc gccgactgtc ggcgctg                                        87

<210> SEQ ID NO 67
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ttcttcggca ccagccagct gagccaattc atggaccaga acaacccgct gtcggggttg    60
acctgcaagc gccgactgtc ggcgctg                                        87

<210> SEQ ID NO 68
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ttcttcggca ccagccagct gagccaattc atggaccaga acaacccgct gtcggggttg    60
accctcaagc gccgactgtc ggcgctg                                        87

<210> SEQ ID NO 69
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
ttcttcggca ccagccagct gagccaattc atggaccaga acaacccgct gtcggggttg    60
acccgcaagc gccgactgtc ggcgctg                                        87

<210> SEQ ID NO 70
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
ttcttcggca ccagccagct gagccaattc atggaccaga acaacccgct gtcggggttg    60
acccagaagc gccgactgtc ggcgctg                                              87

<210> SEQ ID NO 71
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
ttcttcggca ccagccagct gagccaattc atggaccaga acaacccgct gtcggggttg         60
acccaccgcc gactgtcggc gctg                                                84

<210> SEQ ID NO 72
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ttcttcggca ccagccagct gagccaattc atggaccaga acaacccgct gtcggggttg         60
acccacaagc gccaactgtc ggcgctg                                             87

<210> SEQ ID NO 73
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ttcttcggca ccagccagct gagccaattc atggaccaga acaacccgct gtcggggttg         60
acccacaagc gccaactgtc ggcgctg                                             87

<210> SEQ ID NO 74
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
ttcttcggca ccagccagct gagccaattc atggaccaga acaacccgct gtcggggttg         60
acccacaagc gccgactgtt ggcgctg                                             87

<210> SEQ ID NO 75
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ttcttcggca ccagccagct gagccaattc atggaccaga acaacccgct gtcggggttg         60
acccacaagc gccgactgtt cgcgctg                                             87

-continued

```
<210> SEQ ID NO 76
<211> LENGTH: 40
<212> TYPE: DNA
<213> ORGANISM: Mycobacterium tuberculosis
<220> FEATURE:
<221> NAME/KEY: CDS
<222> LOCATION: (1)..(39)

<400> SEQUENCE: 76 gct gtc ggg gtt gac cca caa gcg ccg act gtc ggc gct g      40
Ala Val Gly Val Asp Pro Gln Ala Pro Thr Val Gly Ala
1               5                   10

<210> SEQ ID NO 77
<211> LENGTH: 13
<212> TYPE: PRT
<213> ORGANISM: Mycobacterium tuberculosis

<400> SEQUENCE: 77

Ala Val Gly Val Asp Pro Gln Ala Pro Thr Val Gly Ala
1               5                   10

<210> SEQ ID NO 78
<211> LENGTH: 47
<212> TYPE: DNA
<213> ORGANISM: Mycobacterium tuberculosis
<220> FEATURE:
<221> NAME/KEY: CDS
<222> LOCATION: (3)..(47)

<400> SEQUENCE: 78 tt ctt cgg cac cag cca gct gag cca att cat gga cca gaa caa ccc      47
   Leu Arg His Gln Pro Ala Glu Pro Ile His Gly Pro Glu Gln Pro
     1               5                   10                  15

<210> SEQ ID NO 79
<211> LENGTH: 15
<212> TYPE: PRT
<213> ORGANISM: Mycobacterium tuberculosis

<400> SEQUENCE: 79

Leu Arg His Gln Pro Ala Glu Pro Ile His Gly Pro Glu Gln Pro
1               5                   10                  15

<210> SEQ ID NO 80
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
ttcttcggca ccagccagct gagccaattc atggaccaga acaacccgct gtcggggttg      60
acccacaagc gccgactgtc ggcgctg                                         87
```

MUTATION ANALYSIS

FIELD OF THE INVENTION

The present invention relates to methods and compositions for genomic analysis, and in particular for determining the presence or absence of mutant alleles in a genomic locus.

SEQUENCE LISTING

The instant application contains a Sequence Listing that has been submitted electronically in ASCII format and is hereby incorporated by reference in its entirety. The ASCII copy, created on Jan. 18, 2018, is named 2010183-0011_SL.txt and is 30,758 bytes in size.

CROSS-REFERENCE TO RELATED APPLICATIONS

This application is a National Stage Entry of PCT/GB2014/052939, filed Sep. 30, 2014, which application is hereby incorporated by reference in its entirety.

BACKGROUND TO THE INVENTION

Nucleic acid probes are often used to identify the presence of specific target sequences in genomic or amplified DNA. The annealing or melting temperature of the probe to the target is affected by the length of the complementary region shared by the probe and the target, and by the existence of any mismatches between the otherwise complementary base pairs. This can be used to detect the presence of variants, for example SNPs or multiple repeats. A probe can be designed to have a first melting temperature (Tm) to a wild type sequence, and the annealing of the probe to the target monitored, for example through development of fluorescence on annealing. If the Tm is different to the expected value, then the target sequence includes a variant.

International patent application WO2012/093262 describes methods for detecting and analysing single nucleotide polymorphisms (SNPs) using oligonucleotide probes which hybridise to variant alleles with a lower Tm than that with which they hybridise to wild type alleles. The methods use the polymerase chain reaction (PCR) to amplify a fragment of the genome including the target sequence at a temperature between the first and second Tms. If the target sequence is wild type, then the probe remains bound to the target, and prevents amplification; if the target sequence is a variant, then the probe is not bound to the target, and amplification takes place. In this way, the presence of a variant may be established, and the variant allele selectively enriched in a sample.

International patent application WO2013/041853 describes probes for detecting polymorphisms including SNPs and short tandem repeats (STRs). The probes include first and second regions joined by a linker nucleic acid sequence, such that the first and second regions have independent Tms. The probe sequences may be designed so as to have varying Tm depending on whether a variant or wild type allele is present at a first target region and a second target region. The use of this linker probe allows a single oligonucleotide probe to be used to detect variants in a longer sequence than would otherwise be possible with conventional probes.

However, not all variants are clinically important. In particular, although some mutations may be associated with phenotypic variation (for example, susceptibility to a particular drug), others may be phenotypically neutral or even silent. Silent mutations in particular are those where a mutation in the nucleotide sequence does not give rise to a corresponding mutation in the encoded polypeptide sequence. This is typically the case with mutations in the third base of a particular codon.

The following table, taken from http://en.wikipedia.org/w/index.php?title=Genetic_code&oldid=567109686, shows the genetic code and illustrates the degeneracy of the code and shows which mutations may be phenotypically silent. For example, a mutation from UUU to UUC will still code for phenylalanine, so will have no effect on the expressed protein.

STANDARD GENETIC CODE

| 1st base | 2nd base | | | | | | | | 3rd base |
|---|---|---|---|---|---|---|---|---|---|
| | U | | C | | A | | G | | |
| U | UUU | (Phe/F) | UCU | (Ser/S) | UAU | (Tyr/Y) | UGU | (Cys/C) | U |
| | UUC | Phenylalanine | UCC | Serine | UAC | Tyrosine | UGC | Cysteine | C |
| | UUA | (Leu/L) | UCA | | UAA | Stop (Ochre) | UGA | Stop (Opal) | A |
| | UUG | Leucine | UCG | | UAG | Stop (Amber) | UGG | (Trp/W) Tryptophan | G |
| C | CUU | | CCU | (Pro/P) | CAU | (His/H) | CGU | (Arg/R) | U |
| | CUC | | CCC | Proline | CAC | Histidine | CGC | Arginine | C |
| | CUA | | CCA | | CAA | (Gln/Q) | CGA | | A |
| | CUG | | CCG | | CAG | Glutamine | CGG | | G |
| A | AUU | (Ile/I) | ACU | (Thr/T) | AAU | (Asn/N) | AGU | (Ser/S) | U |
| | AUC | Isoleucine | ACC | Threonine | AAC | Asparagine | AGC | Serine | C |
| | AUA | | ACA | — | AAA | (Lys/K) | AGA | (Arg/R) | A |
| | AUG | (Met/M) Methionine | ACG | | AAG | Lysine | AGG | Arginine | G |
| G | GUU | (Val/V) | GCU | (Ala/A) | GAU | (Asp/D) | GGU | (Gly/G) | U |
| | GUC | Valine | GCC | Alanine | GAC | Aspartic acid | GGC | Glycine | C |
| | GUA | | GCA | | GAA | (Glu/E) | GGA | | A |
| | GUG | | GCG | | GAG | Glutamic acid | GGG | | G |

Other mutations may have some effect on the expressed protein sequence, but still no clinical effect, for example, by substituting one amino acid with a functionally similar amino acid.

Current detection methods are either specific for one particular mutation, so cannot be used more generally where multiple possible mutations may be present, or are sensitive to any mutation, so will identify nonsignificant mutations as well as clinically significant ones.

It would be desirable to have a method whereby nonsignificant mutations will not be detected, but which is still sensitive enough to identify a range of other mutations.

BRIEF SUMMARY OF THE INVENTION

According to a first aspect of the present invention, there is provided a method for detecting the presence of a variant nucleic acid sequence in a polymorphic target nucleic acid sequence, the target sequence being present in multiple alleles within a given population, the method comprising a) providing a reaction mix comprising an oligonucleotide probe having a first melting temperature (Tm) when hybridised to a first allele of the target sequence, and a second lower Tm when hybridised to a second allele of the target sequence, wherein the probe comprises at least one universal base at a site where variants are not desired to be detected; and a target nucleic acid sequence;

b) allowing the probe to hybridise to a target nucleic acid sequence; and c) determining the Tm of the probe when hybridised to the target nucleic acid sequence;

to thereby determine whether a variant nucleic acid sequence is present.

A universal base is one which is able to form Watson-Crick base pairs with any of the four canonical nucleic acid bases (A, C, G, T). Examples of universal bases include 2'-deoxyinosine (hypoxanthine deoxynucleotide) derivatives, nitroazole analogues, and hydrophobic aromatic non-hydrogen-bonding bases. Preferred universal bases for use in the present invention include d-inosine and 5-nitroindole.

The site where variants are not desired to be detected is preferably a residue where mutations are phenotypically silent mutations (for example, typically the third base in a codon where the mutation does not change the expressed amino acid); or it may be a residue where mutations do change the peptide sequence but give rise to conservative replacements which do not alter the properties of the expressed peptide. Of course, it is also possible to use the methods of the present invention to suppress detection of any desired mutation; it need not be a silent mutation.

In this way, the probe will hybridise to alleles which differ only at the corresponding residue to the universal base with the same Tm. An altered Tm is only seen when the alleles differ at residues where there is no universal base; in this way detection of the presence of certain mutations may be suppressed without altering the ability of the probe to detect a range of different mutations.

In some embodiments, the probe may comprise more than one universal base at a site where variants are not desired to be detected. More than one such sites may also or instead be present in the probe.

The first allele may be designated the wild type; and the second allele may encompass multiple variants (for example, multiple different SNPs, as well as multiple SNPs within a single variant allele), provided the relative Tms of the probe when hybridised to first and second alleles is as set out above.

Preferably the probe is DNA.

The differences in sequence between the first and second alleles are preferably internal to the region where the probe binds; that is, any mismatches between the probe and the first allele are not at the ends of the probe.

The probe may be up to 10, 20, 30, 40, or 50 nucleotides in length. Longer or shorter probes are possible, although it may be difficult to attain suitable discrimination between Tm for different alleles or with the Tm of the primers with shorter probes.

The step of determining the Tm of the probe may further comprise comparing the Tm of the probe to an expected Tm, in order to determine whether the allele is a variant allele.

Step c), determining the Tm of the probe when hybridised to the target nucleic acid sequence, may comprise the step of detecting hybridisation of the probe to the target at a first temperature at or below the second Tm, and detecting hybridisation at a second temperature at or below the first Tm, but above the second Tm.

The probe may be labelled. For example, the probe may include a fluorescent or a radioactive label, or may be labelled with a ligand to which a secondary probe may bind. Preferably the probe is labelled with a fluorescent label, and preferably also the label generates a differential signal depending on whether the probe has hybridised to a target strand (that is, the probe is part of a double stranded nucleic acid) or not (the probe is single stranded). A preferred probe is a HyBeacon® probe (see, for example, Mol Cell Probes. 2002 October; 16(5):319-26, "Ultra-rapid DNA analysis using HyBeacon probes and direct PCR amplification from saliva", French D J, Archard C L, Andersen M T, McDowell D G). Generation of differential signals allows easy and rapid analysis of whether the probe has bound to a target.

The method may further comprise the step of preferentially amplifying the second allele of the target sequence. This may include, prior to step c), steps of:

b2) providing to the reaction mix a pair of oligonucleotide primers for nucleic acid amplification, the primers hybridising to the nucleic acid at first and second sites flanking the oligonucleotide probe binding site; wherein the Tm of the primer: sample is higher than the Tm of the probe: second allele;

b3) maintaining the reaction mix at a temperature between the probe: first allele Tm and the probe: second allele Tm, such that the probe preferentially hybridises to the first allele;

b4) carrying out a thermal cycling amplification on the reaction mix, the amplification including a melt phase, an annealing phase, and an extension phase, in which the temperatures of the extension and annealing phases are between the probe: first allele Tm and the probe: second allele Tm, such that the probe is hybridised to the first allele during these phases; to thereby amplify the second allele; and wherein step c) comprises detecting hybridisation of the probe to the sample at a temperature at or below the probe: second allele Tm; detecting hybridisation of the probe to the sample at a higher temperature at or below the probe: first allele Tm; and comparing the two; to thereby detect the amplified second allele.

This allows the universal base probe to be used in selectively amplifying an allele prior to detecting and determining the Tm. This can be used to enrich a sample which may have only a few copies of the second allele. The probe is used initially to block amplification of the first allele by remaining bound to the first allele during the extension phase, and then to detect the allele after amplification. During the extension phase, the oligonucleotide probe remains hybridised to the first allele. This prevents strand extension of the primer hybridised to the same nucleic acid, whereas primers hybridised to the second allele are free to undergo strand extension since the probe is not hybridised to that allele. In this way, the second allele will be preferentially amplified. In certain embodiments one or both of the primers may overlap with the probe binding site such that the probe competes with the primer for binding; this can prevent binding of the primer and hence strand extension. In other embodiments the primers and probe do not overlap, but the primer prevents further strand extension.

The step of detecting hybridised probe molecules may further comprise quantification of the relative amounts of first and second alleles in the amplification mix. In certain embodiments of the invention, a detection step may be carried out before as well as after the amplification step. In a preferred embodiment, the ratio of first to second alleles may be measured by: maintaining the reaction mix at a first temperature at or below the Tm of the probe: second allele; detecting hybridised probe molecules; increasing the reaction mix to a second temperature above the Tm of the probe: second allele but at or below the Tm of the probe: first allele; and detecting hybridised probe molecules. At the first, lower temperature, probe will be hybridised to both first and second alleles, while at the second higher temperature, probe will be hybridised only to the first allele.

The primers preferably bind at a region outside the region where the probe binds; that is, a first primer binds 3'-wards of the probe target, while a second primer binds 5'-wards of the probe target (bearing in mind that the primers will bind to different strands of the duplex DNA). When the primers undergo strand extension, this is blocked by the bound probe, such that the strand cannot be amplified. In certain embodiments the primers may bind adjacent to the region where the probe binds, or may even overlap with the probe by one, two, three, or more nucleotides, although this is not preferred. Of course, the two primers may overlap with the probe target to different extents, or one may overlap and the other may not. Where the probe and the primer overlap, then the probe may compete with the primer for binding, preferably at the 3' end of the primer, and prevent extension in this way.

In preferred embodiments of the invention, the amplification reaction is polymerase chain reaction (PCR). In certain embodiments, the primers may be provided in different concentrations; preferably one of the primers is provided in a rate-limiting amount, and the amplification reaction is asymmetric PCR. In asymmetric PCR, one of the two target DNA strands is preferentially amplified, as the rate-limiting primer is used up so only the other primer is available to begin strand extension. Either the sense or the antisense strand may be the one targeted for preferential amplification; preferably the preferentially amplified strand is the complementary strand to the probe.

The probe may comprise one, two, three, four, five, or more universal bases.

In certain embodiments, the probe may comprise a first nucleic acid sequence being complementary to a first target nucleic acid sequence; a second nucleic acid sequence being complementary to a second target nucleic acid sequence; and a linker nucleic acid sequence joining the first and second nucleic acid sequences; wherein the linker separates the two first and second sequences such that the melting temperature of the first sequence annealed to the first target nucleic acid sequence and of the second sequence annealed to the second target nucleic acid sequence are discrete.

The presence of the linker region allows the probes to be split into functional elements that have different hybridisation characteristics. Inclusion of these linkers creates 'bubble' structures, isolating the elements of the probe from a thermodynamic perspective, to provide regions with different binding characteristics. Further, the presence of the linker nucleic acid sequence allows the whole probe to have the characteristics of a single polynucleotide molecule, but to behave as if composed of separate shorter nucleic acid probes. The linker region may fold to form a loop out when the first and second sequences hybridise to their respective target sequences.

The probe structure allows probing of contiguous regions, where longer probes (for example, a single probe spanning both first and second target regions) would not provide adequate reporting through Tm analysis to differentiate variants. Preferably, therefore, the first and second target nucleic acid sequences are contiguous.

Preferably the linker is a nucleoside linker; more preferably the linker comprises polydeoxyribonucleotides; most preferably the linker comprises or consists of polydeoxyinosine. Deoxyinosine has a low melting temperature relative to natural bases due to weaker hydrogen bonding. Other nucleosides may be used.

Preferably the linker is up to 5, 10, 15, 20, 30, 40, 50 nucleotides in length.

At least one of the first and second nucleic acid sequences is a reporter region. A reporter region includes a labelled moiety; preferably a fluorescent label. This allows detection of the probe in the event of binding to a target sequence, and monitoring of annealing over a temperature range in order to determine the presence of any variant target sequences.

The probe preferably does not comprise a quencher moiety, nor is the label intended to be used with a quencher. Suitable labels include FAM, TET, HEX, ROX, TAMRA, Cy3, and Cy5. Other suitable labels will be known to the skilled person. Preferably the label is incorporated on to a T nucleotide, although any suitable nucleotide may be used.

The reporter region is preferably 15-200 nt in length, more preferably 15-150, more preferably still 15-100, or 20-100, 30-80, 40-60, or around 50 nt in length.

The reporter region may further comprise a blocking region; that is, a portion which serves to block extension of the nucleic acid strand by DNA polymerase, so preventing strand extension during, for example, PCR. A polymerase enzyme blocking group is one which should have the functional properties of blocking further elongation of the polymer. A blocking group may be any chemical group which can be attached to a nucleotide which will allow the 5' end of the modified nucleotide to attach to a 3' end of another nucleotide in a DNA chain but will not allow attachment of a nucleotide to the 3'hydroxyl group of the modified nucleotide. Suitably, the absence of an OH group in the 3' position will prevent further elongation by polymerase activity. In a particularly preferred embodiment, the blocking group is selected from acetyl, $CH_3$, glycyl, leucyl and alanyl groups. In another embodiment, the blocking group may be in the form of a di or tri peptide.

In a preferred embodiment of the invention, both the first and second nucleic acid sequences are reporter regions. They may include different labels. Such a probe may be used as a multiplex reporter, allowing detection of target sequences over an extended range with a single probe.

In certain embodiments of the invention, a plurality of oligonucleotide probes may be provided, preferably two. The probes may either or both comprise at least one universal base; preferably both comprise at least one universal base. The probes are preferably selected to hybridise to contiguous portions of the target sequence. This allows a greater effective "read length" of the target without the limitations of having to provide a single long probe. Further, the ability to effectively detect contiguous portions of the target sequence is unexpected, as the skilled person might expect that two adjacent probes may interfere with one another, particularly in the case where chemical modifications (such as extension blockers, or labels) are present on the 3' and/or 5' ends of the probes.

In preferred embodiments of the invention, where a plurality of oligonucleotide probes are provided, all (preferably both) are "linker probes" as referred to above; that is, comprising first and second nucleic acid sequences complementary to first and second target sequences, joined by a linker nucleic acid sequence. Such an arrangement provides for detection of variant sequences across a relatively long section of target, and balances size of probe against size of target.

The target sequence may be a portion of a microbial drug resistance gene. In a preferred embodiment, the target sequence is a *Mycobacterium tuberculosis* gene, preferably rpoB. This gene is responsible for rifampin resistance. In other embodiments, the target sequence may be a patient's own gene, for example, to determine susceptibility to certain drugs or other treatments, or to diagnose genetic conditions.

According to a further aspect of the invention, there is provided an oligonucleotide probe having a first melting temperature (Tm) when hybridised to a first allele of a target sequence, and a second lower Tm when hybridised to a second allele of a target sequence, wherein the probe comprises at least one universal base at a site where variants are not desired to be detected.

Examples of universal bases include 2'-deoxyinosine (hypoxanthine deoxynucleotide) derivatives, nitroazole analogues, and hydrophobic aromatic non-hydrogen-bonding bases. Preferred universal bases for use in the present invention include d-inosine and 5-nitroindole.

The site where variants are not desired to be detected is preferably a residue where mutations are phenotypically silent mutations (for example, typically the third base in a codon where the mutation does not change the expressed amino acid); or it may be a residue where mutations do change the peptide sequence but give rise to conservative replacements which do not alter the properties of the expressed peptide.

In some embodiments, the probe may comprise more than one universal base at a site where variants are not desired to be detected. More than one such sites may also or instead be present in the probe.

Preferably the probe is DNA.

The probe may be labelled. For example, the probe may include a fluorescent or a radioactive label, or may be labelled with a ligand to which a secondary probe may bind. Preferably the probe is labelled with a fluorescent label, and preferably also the label generates a differential signal depending on whether the probe has hybridised to a target strand (that is, the probe is part of a double stranded nucleic acid) or not (the probe is single stranded). A preferred probe is a HyBeacon® probe (see, for example, Mol Cell Probes. 2002 October; 16(5):319-26, "Ultra-rapid DNA analysis using HyBeacon probes and direct PCR amplification from saliva", French D J, Archard C L, Andersen M T, McDowell D G).

The probe may comprise one, two, three, four, five, or more universal bases.

In certain embodiments, the probe may comprise a first nucleic acid sequence being complementary to a first target nucleic acid sequence; a second nucleic acid sequence being complementary to a second target nucleic acid sequence; and a linker nucleic acid sequence joining the first and second nucleic acid sequences; wherein the linker separates the two first and second sequences such that the melting temperature of the first sequence annealed to the first target nucleic acid sequence and of the second sequence annealed to the second target nucleic acid sequence are discrete.

Preferably the linker is a nucleoside linker; more preferably the linker comprises polydeoxyribonucleotides; most preferably the linker comprises or consists of polydeoxyinosine. Deoxyinosine has a low melting temperature relative to natural bases due to weaker hydrogen bonding. Other nucleosides may be used.

Preferably the linker is up to 5, 10, 15, 20, 30, 40, 50 nucleotides in length.

At least one of the first and second nucleic acid sequences is a reporter region. A reporter region includes a labelled moiety; preferably a fluorescent label. This allows detection of the probe in the event of binding to a target sequence, and monitoring of annealing over a temperature range in order to determine the presence of any variant target sequences. The probe preferably does not comprise a quencher moiety, nor is the label intended to be used with a quencher. Suitable labels include FAM, TET, HEX, ROX, TAMRA, Cy3, and Cy5. Other suitable labels will be known to the skilled person. Preferably the label is incorporated on to a T nucleotide, although any suitable nucleotide may be used.

The reporter region is preferably 15-200 nt in length, more preferably 15-150, more preferably still 15-100, or 20-100, 30-80, 40-60, or around 50 nt in length.

The reporter region may further comprise a blocking region; that is, a portion which serves to block extension of the nucleic acid strand by DNA polymerase, so preventing strand extension during, for example, PCR. A polymerase enzyme blocking group is one which should have the functional properties of blocking further elongation of the polymer. A blocking group may be any chemical group which can be attached to a nucleotide which will allow the 5' end of the modified nucleotide to attach to a 3' end of another nucleotide in a DNA chain but will not allow attachment of a nucleotide to the 3'hydroxyl group of the modified nucleotide. Suitably, the absence of an OH group in the 3' position will prevent further elongation by polymerase activity. In a particularly preferred embodiment, the blocking group is selected from acetyl, $CH_3$, glycyl, leucyl and alanyl groups. In another embodiment, the blocking group may be in the form of a di or tri peptide.

In a preferred embodiment of the invention, both the first and second nucleic acid sequences are reporter regions. They may include different labels. Such a probe may be used as a multiplex reporter, allowing detection of target sequences over an extended range with a single probe.

In certain embodiments of the invention, a plurality of oligonucleotide probes may be provided, preferably two. The probes may either or both comprise at least one universal base; preferably both comprise at least one universal base. The probes are preferably selected to hybridise to contiguous portions of the target sequence. In preferred embodiments of the invention, where a plurality of oligonucleotide probes are provided, all (preferably both) are "linker probes" as referred to above; that is, comprising first and second nucleic acid sequences complementary to first and second target sequences, joined by a linker nucleic acid sequence.

The target sequence may be a portion of a microbial drug resistance gene. In a preferred embodiment, the target sequence is a *Mycobacterium tuberculosis* gene, preferably rpoB. This gene is responsible for rifampin resistance. In other embodiments, the target sequence may be a patient's own gene, for example, to determine susceptibility to certain drugs or other treatments, or to diagnose genetic conditions.

In certain embodiments of the invention, the probe may comprise a sequence selected from SEQ ID NO 5 to SEQ ID NO 10, or may comprise a modified version of such sequences or a modified version of a sequence selected from SEQ ID NO 1 to SEQ ID NO 4. By "modified version" is meant a sequence which differs by deletion or addition of one, two, or three nucleotides; or by substitution of one, two, three, four, five, six, seven, or eight nucleotides (including substitution of standard nucleotides with nonstandard nucleotides, for example universal bases or alternative bases); or both. A modified version may also or instead include a linker sequence of different length and/or composition; an alternative fluorescent label; or an alternative universal base.

A further aspect of the invention provides a plurality of oligonucleotide probes, as described above.

A yet further aspect of the invention provides a kit comprising one or more oligonucleotide probes, as described above, and a primer pair flanking the target nucleic acid site to which the probe(s) hybridise.

BRIEF DESCRIPTION OF THE DRAWINGS

FIG. 2 shows the consensus sequence of the core of the rpoB gene, from codons 505 to 533, together with individual mutants (SEQ ID NOS 80 and 17-75, respectively, in order of appearance).

FIG. 3 shows the position on the core of the rpoB gene of the two linker probes used in the current examples, spanning codons 507-520, and 521-533 (SEQ ID NOS 17 and 76-79, respectively, in order of appearance).

FIG. 5 shows sequences of the linker probes used in the current examples (SEQ ID NOS 13-16 and 1-6, respectively, in order of appearance).

FIG. 9 shows detection of results from low copy number samples.

DETAILED DESCRIPTION OF THE INVENTION

Figure 1:
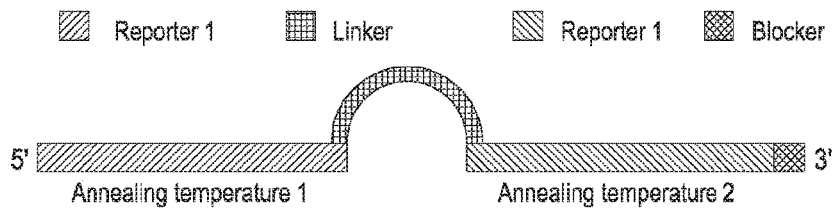
FIG. 1 shows a schematic of the probe construction (taken from WO2013/041853)

Referring first of all to FIG. 1, this shows the general structure of probes as used in the present invention. The probes consist of three regions: a first reporter sequence, having homology to a first target sequence; a linker sequence, in this instance comprising five inosine nucleobases; and a second reporter sequence, having homology to a second target sequence. The second reporter also includes, at the 3' end, a blocking sequence which will prevent strand extension during polymerisation reactions. Each reporter region has different annealing temperatures and has 1 or more fluorescent nucleotides, preferably FAM-T, or different/multiple colours. The reporter is used to report the presence of a specific sequence or sequence variants (eg, SNPs, insertions, deletions, etc). This allows multiple sequences over an extended range to be detected with a single probe. Each region is tuned to have a similar (or identical) Tm in the case of the wild type sequence, but a shifted Tm in the case of a mutation so that a user only has to detect the shifted Tm to know the variant is present. By "similar" is meant that the Tm differs by at most 2, 1.5, 1, 0.5 deg C.

An example of use of multiplexed reporter probes to detect variants in the *Mycobacterium tuberculosis* rpoB gene is now given. Multi drug resistance in *M. tuberculosis* is complex. Rifampin is a first line *M. tuberculosis* medication and is the main target to identify in the field prior to treatment. Rifampin resistant *M. tuberculosis* have mutations in the 81-bp core region of the rpoB gene, which encodes the β-subunit of RNA polymerase. 96% of Rifampin resistant clinical isolates of *M. tuberculosis* have mutations in this gene. Mutations in codons 516, 526, or 531 result in high level Rifampin resistance. However, detecting mutations across an 81-bp gene region would typically require multiple conventional probes, several of which would need to overlap, so requiring multiple detection steps.

Using linker probes as described goes some way towards addressing this problem, but still leaves open the issue that some mutations will be phenotypically silent, having no effect on drug resistance. Accordingly, the present invention makes use of linker probes incorporating universal bases in order to prevent detection of such silent mutations, while still being able to detect desired mutations with a high sensitivity.

Figure 2:
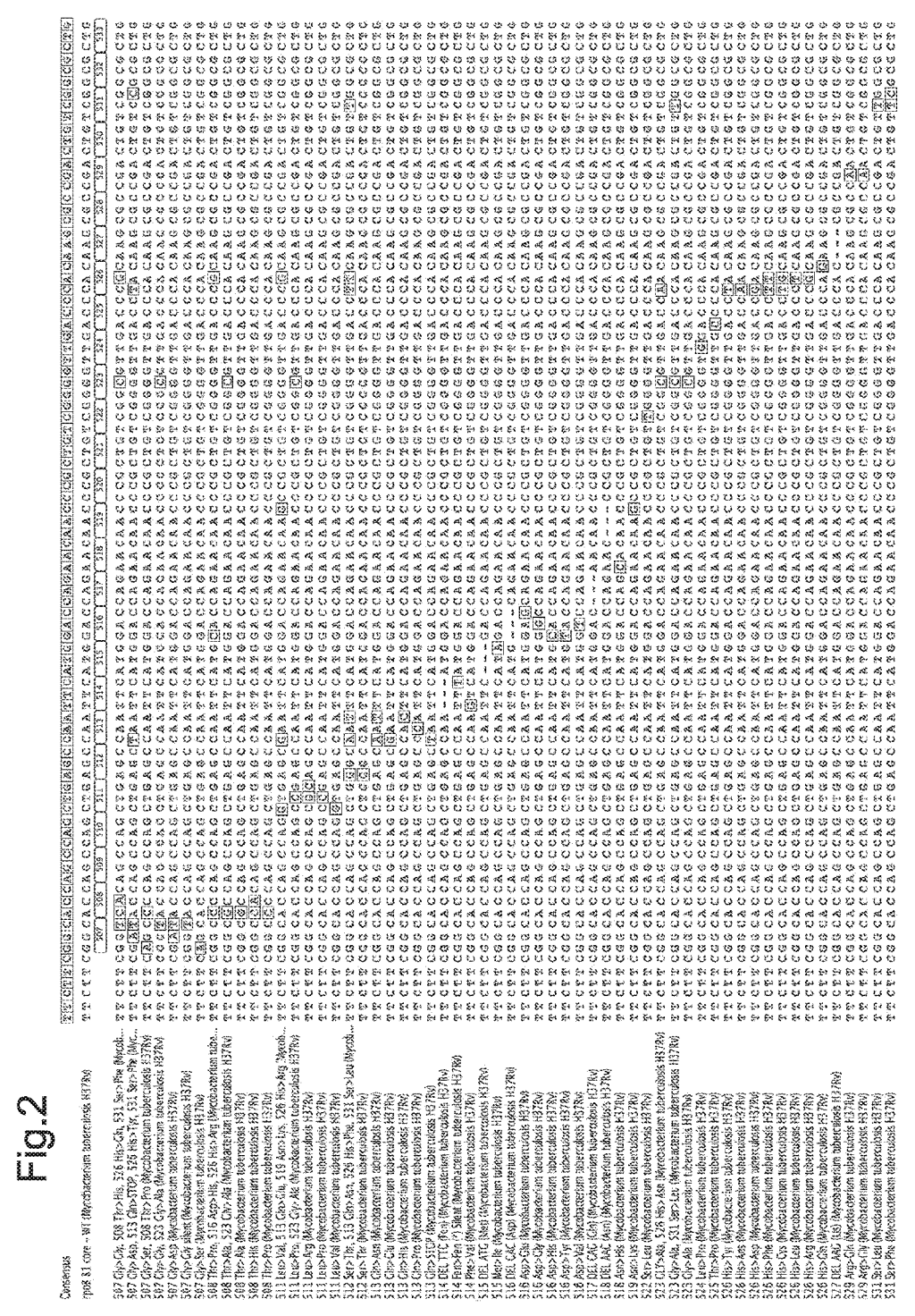

FIG. 2 shows the wild type consensus sequence from codons 505 to 533 of the rpoB gene, together with known mutations (silent and non-silent) in this region. It is apparent that there are a large number of known mutations, and sensitive detection of silent ones would risk the selectivity (and usefulness) of a diagnostic test for the important mutations.

Figure 3:
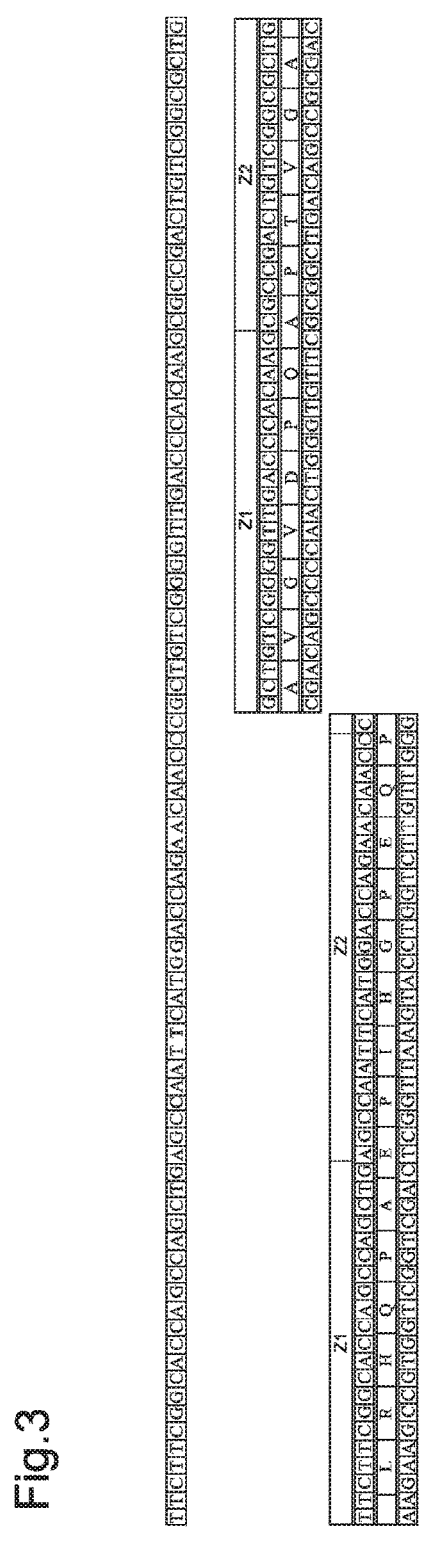

In order to demonstrate the principles of the present invention, two linker probes were synthesised covering a 90 bp region spanning codons 507-520 and 520-533 of the MTB rpoB gene. Oligonucleotides were made using the cyanoethylphosphoramidite method. The location of the probes against the genomic sequence is shown in FIG. 3. The two reporter domains of the probes are labelled as Z1 and Z2; these are joined in each probe by a linker (not shown in FIG. 3). The 3' end of each probe includes a blocker group. Note that the two linker probes cover adjoining regions of the genomic sequence.

Using unmodified probes having the sequence noted in FIG. 3, it is possible to detect the presence of mutations in a target sequence by virtue of changes in melting temperature arising from mismatches between the probe sequence and the target sequence. Single base mismatches can be detected with high sensitivity. See, for example, international patent application WO2013/041853, which describes use of similar probes (although only individual probes, not pairs of adjacent probes) to detect SNP mutations in the rpoB gene.

Figure 4:
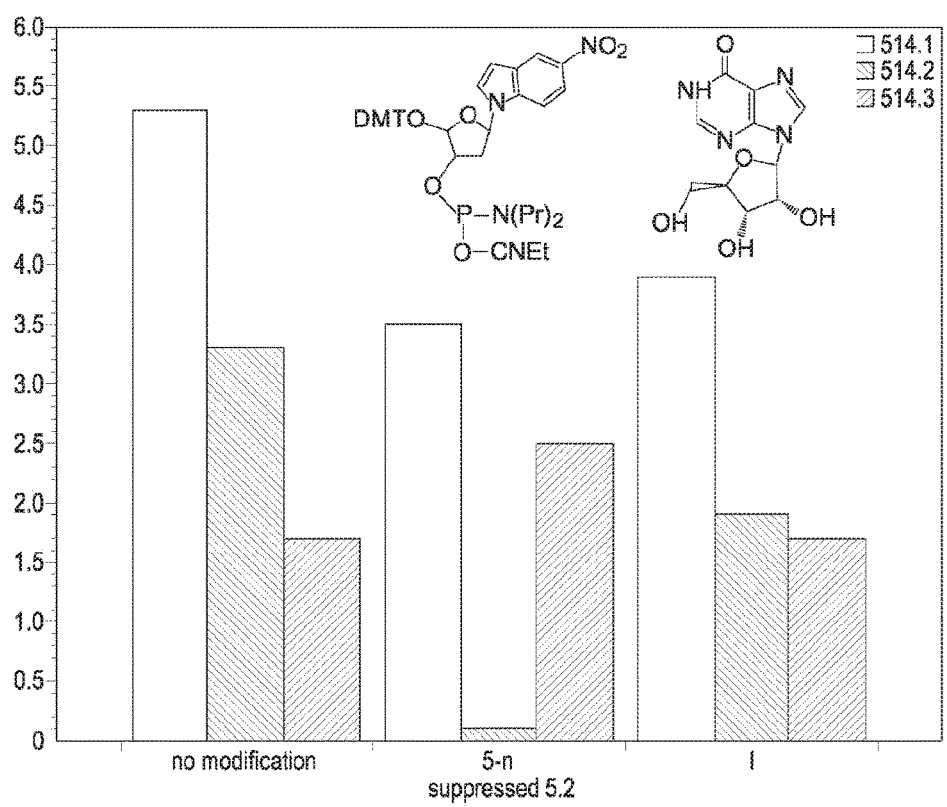
FIG. 4 shows the structure of the universal base 5-nitroindole-CE phosphoramidite.
Figure 6:
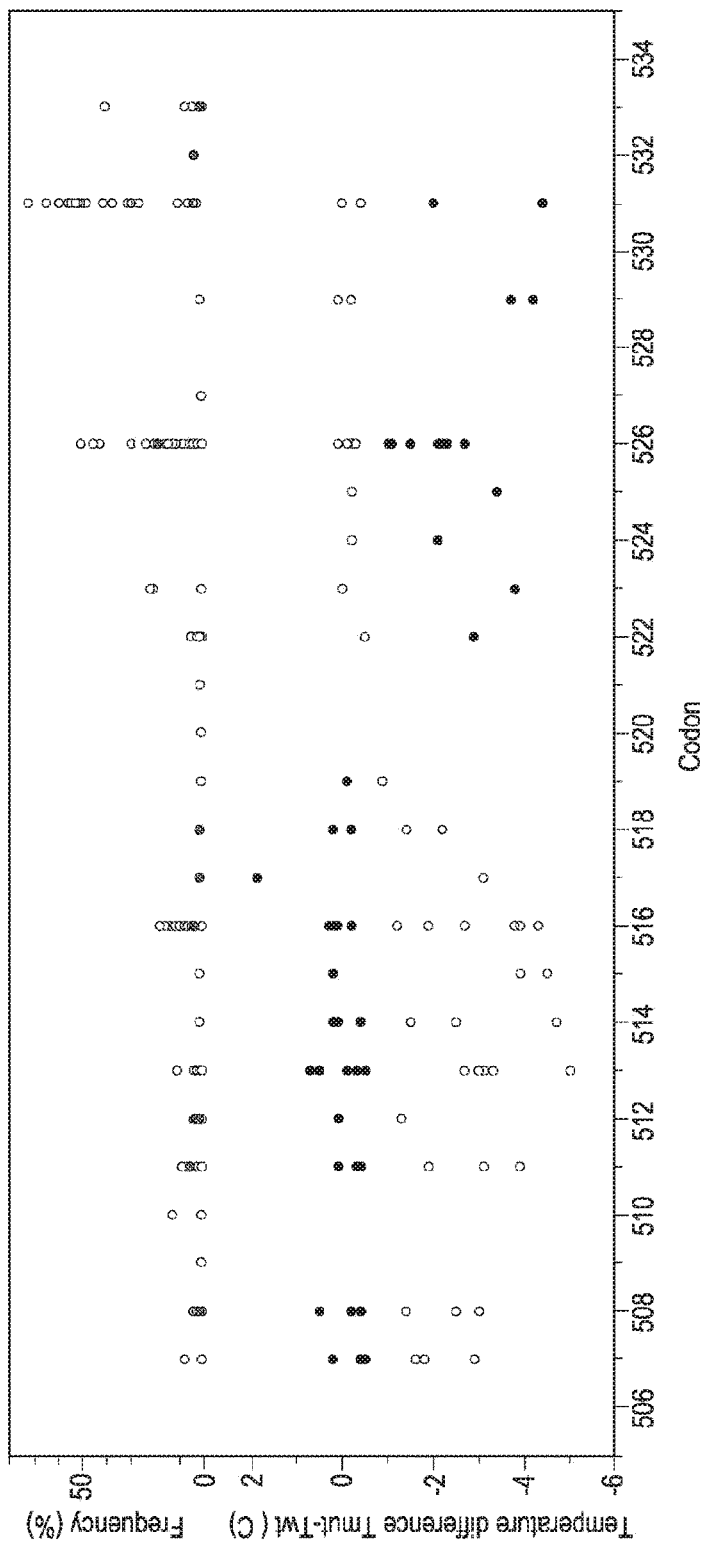
FIG. 6 shows detection of a shift in melting temperatures of linker probes when used against template rpoB sequences with mutations.
Figure 7:
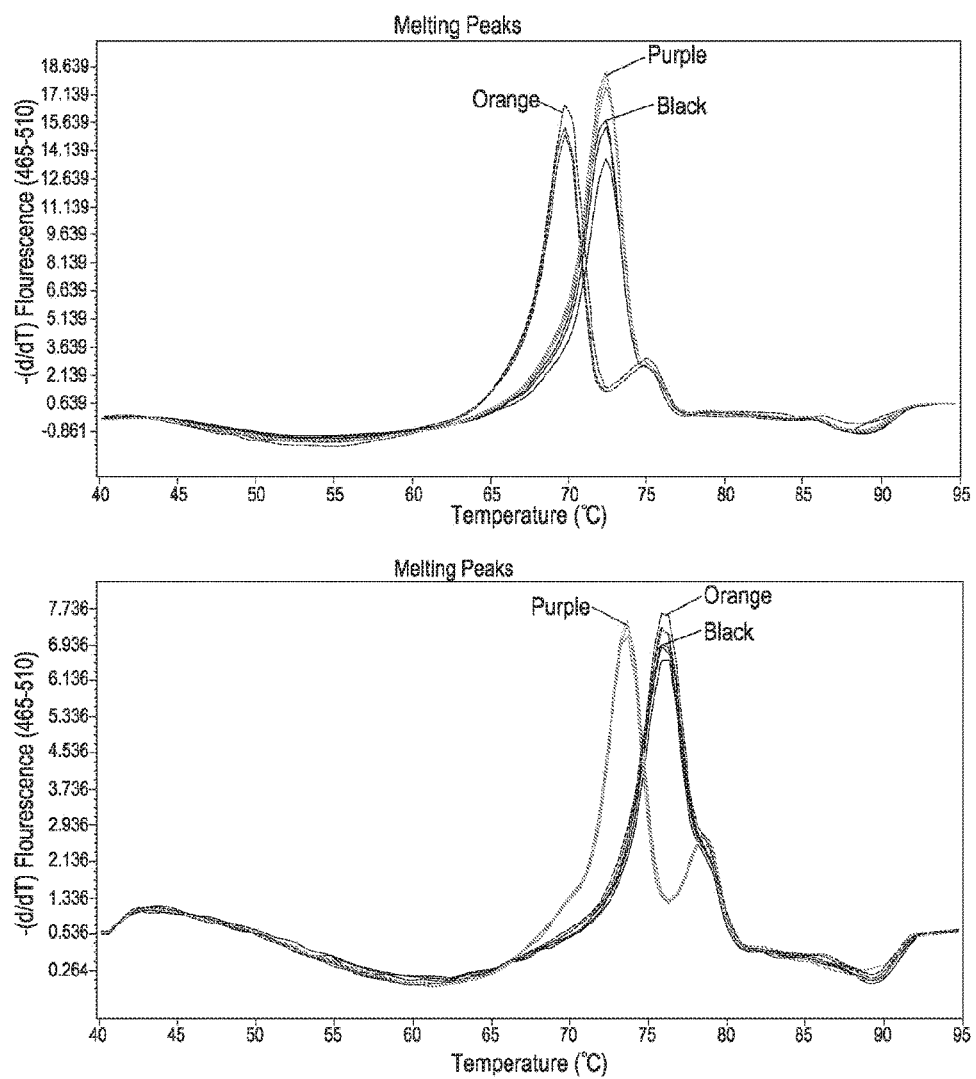
FIG. 7 shows representative melt curves from the reactions of FIG. 6.
Figure 8:
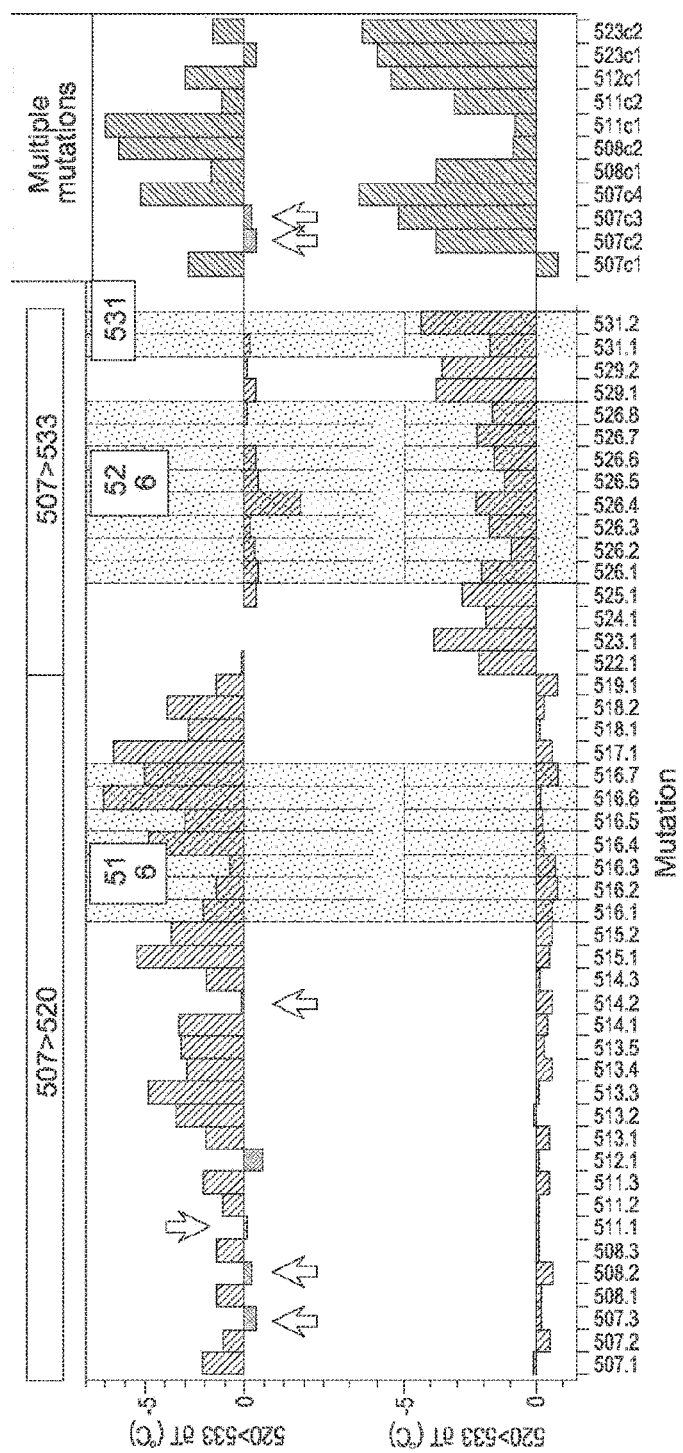
FIG. 8 shows observed shift in melting temperatures observed for mutations in codons 507-533 using the two linker probes in combination.

The aim of the experiments described herein was to investigate the possibility of suppressing detection of mutations at selected positions. To this end, the universal base 5-nitroindole-CE phosphoramidite (Glen Research; FIG. 4) was used to cancel the effects of mutations on the melt curve destabilisation with the view of preventing phenotypically silent mutations from being called. A total of 4 codons were identified as having an agnostic third base in codons 507>520 and these bases were substituted with either 5-nitrolindole or d-inosine to investigate the effects of this base on neutralising the destabilisation effect.

The sequences of the probes are given in FIG. 5. In the Figure, the standard DNA bases have the usual symbols (A, C, G, T), and nonstandard bases or modifications are indicated with numbers: 1=fluorescein dT; 2=phosphate block; 3=trimethoxystilbene; 4=5-nitroindole; *=Inosine residues (5 per probe). The various probes are as follows:

rpoB (507>520) Linked-Probe (SEQ ID NO 13)—the labelled probe including a linker, fluorescent residues, and a blocker, covering codons 507-520.

rpoB (507>520) (SEQ ID NO 14)—a labelled nucleotide probe spanning codons 507-520, with no linker or blocker.

rpoB (520>533) Linked-Probe (SEQ ID NO 15)—the labelled probe including a linker, fluorescent residues, and a blocker, covering codons 521-533 rpoB (520>533) (SEQ ID NO 16)—a labelled nucleotide probe spanning codons 521-533, with no linker or blocker.

rpoB (507>520)_silent_1 (SEQ ID NO 1)—a labelled probe including a linker, fluorescent residues, and a blocker, with a single silent mutation replaced with 5-nitroindole in each reporter portion of the probe, covering codons 507-520.

rpoB (507>520)_short (SEQ ID NO 2)—a shorter version of rpoB (507>520)_silent_1.

rpoB (520>533)_silence_all (SEQ ID NO 3)—a labelled probe including a linker, fluorescent residues, and a blocker, with four silent mutations replaced with 5-nitroindole in each reporter portion of the probe, covering codons 521-533.

rpoB (507>520)_silence_all (SEQ ID NO 4)—a labelled probe including a linker, fluorescent residues, and a blocker, with all silent mutations replaced with 5-nitroindole in each reporter portion of the probe, covering codons 507-520.

rpoB (507>520)_shortA (SEQ ID NO 5)—a shorter version of rpoB (507>520)_silent_1.

rpoB (507>520)_shortB (SEQ ID NO 6)—a shorter version of rpoB (507>520)_silence_all.

Primers used for PCR amplification of target rpoB sequences from samples are shown below:

```
FWD primer v1
(5' > 3')
                              (SEQ ID NO 11)
GCAGACGTTGATCAACATCC FWD primer v2
(5' > 3')
                              (SEQ ID NO 12)
CGTGGAGGCGATCACACCGCAGACGTT.
```

Results

Samples containing rpoB were amplified using the primers, and subjected to melt curve analysis with both the rpoB (507>520) Linked Probe probe and the rpoB (520>533) Linked probe (neither include silenced mutation sites). Data shows that single and multiple mutations were detectable as a shift in the melting temperature of the probe (FIGS. 6 & 7). FIG. 6 (upper chart) shows the frequency of mutations at each codon reported in the literature. Red (filled) dots indicate the frequency of these mutations in India. The lower plot of FIG. 6 shows the effect of mutations in codons between 507>520 on the 507>520 probe, and in codons between 520>533 on the 520>533 probe, on the reported melt temperature as a deviation from WT.

The reported TM for probe rpoB (520>533) Linked probe in templates where mutations are present in codons 507-520 and therefore not reported by the probe and represented by a peak at 77.5° C.±0.27° C., compared to templates with mutations present in codons 520-533 and therefore represented by a shift in TM with an average TM of 74.8° C.±1.14° C.

Representative melt curves are shown in FIG. 7, which gives melt curve analysis of rpoB mutations in rpoB from clinical RRDR isolates D516V (top) and N531L (bottom) using separated probes. In the top chart where the probe covering codons 507>520 was used, the D516V template (orange, left hand peak) is reported with a peak at 69.9° C. compared to N531L (purple, right hand peak) whose mutation falls outside of the probe range and is reported at the wild type (black, right hand peak) position for that probe of 72.2° C. Conversely, where the same templates are used in conjunction with probe covering 520>533 the reported position for D516V (orange, right hand peak) is wild type (black, right hand peak) 75.9° C. compared to the N531L mutant (purple, left hand peak) which is reported at position 73.5° C.).

The substitution of bases resulting in a wild type phenotype (silent mutations) with 5-nitroindole was shown to cancel the destabilization effect. Both mutations in 507 and 514 shown previously to be silent but detectable with conventional SNP probes were completely neutralized (FIG. 7). A potential 10 positions could be neutralized in 520>533 using the same methodology if required.

FIG. 8 shows the variation in Tm seen with a range of different SNP or multiple mutations across the rpoB gene using a combination of both fully silenced probe rpoB (507>520) silence_all, and the non-silenced probe rpoB (520>533) Linked-Probe. It is apparent that the silenced mutations 507.3, 508.2, 512.1, and 514.2 preserve the Tm within the wild type range, whereas other, non-silenced, mutations show a larger variation in Tm compared with the wild type. This confirms that the methodology and the probes are robust.

FIG. 8 shows the effect of mutations in codons between 507>520 on the 507>520 probe, and in codons between 520>533 on the 520>533 probe. The shift is suppressed at positions corresponding to the phenotypically silent mutations where the base has been substituted with 5-nitroindole. Templates that have multiple mutations are also shown leading to a shift in the reported position of both probes, or again where 5-nitroindole is substituted at the base corresponding to a silent mutation the shift is silenced to allow the correct phenotypic reporting.

Multiple mutations were associated with an increased shift in TM with increasing number of mismatches. Deletions were also detected with a large shift in TM.

The assay was highly sensitive using samples of as few as 100 (top) or 10 (bottom) (FIG. 9). It enables detection of mutations in all codons including the key mutations in codons 516, 526, 531 and 533 and additionally neutralizes the effect of silent mutations in codons 507 and 514 that have previously been reported as problematic in alternative products.

We believe that this set of two Linked-Probes represents a sensitive and state-of-the-art test for RIF-mutation detection and that the methodology is equally applicable to other genomic loci.

The invention claimed is:

1. A method for detecting the presence of a variant nucleic acid sequence in a target nucleic acid sequence that is polymorphic in that it is present in multiple alleles within a given population, the method comprising
  a) providing a reaction mix comprising:
    an oligonucleotide probe that hybridizes to the target nucleic acid sequence at a region where individual alleles within the multiple alleles differ from one another, which region includes a first site where individual alleles within the multiple alleles differ by at least one non-silent mutation desired to be detected and also includes a second site where individual alleles within the multiple alleles differ by at least one phenotypically silent mutation or conservative mutation not desired to be detected, wherein the oligonucleotide probe has a first melting temperature (Tm) when hybridized to a first allele of the target sequence, which first allele includes the non-silent mutation at the first site, and a second, different Tm when hybridized to a second allele of the target sequence, which second allele does not include the non-silent mutation at the first site, and further wherein the probe comprises at least one universal base at the second site where variants are not desired to be detected, and wherein the site where variants are not desired to be detected is a residue where mutations are phenotypically silent mutations or is a residue where mutations give rise to conservative replacements which do not alter the properties of the expressed peptide, and wherein the probe does not include a quencher moiety; and a sample comprising nucleic acid whose nucleotide sequence comprises the target sequence;

b) allowing the probe to hybridize to nucleic acids in the sample; and c) determining the Tm of the probe when hybridized to the nucleic acids in the sample;

to thereby determine whether a variant nucleic acid sequence is present in the sample.

2. The method of claim 1, wherein the universal base is selected from d-inosine, 5-nitroindole, 2'-deoxyinosine (hypoxanthine deoxynucleotide) derivatives, nitroazole analogues, and hydrophobic aromatic non-hydrogen-bonding bases.

3. The method of claim 1 wherein the step of determining the Tm of the probe comprises comparing the determined Tm to an expected Tm.

4. The method of claim 1 wherein the step of determining the Tm of the probe comprises steps of:
detecting hybridization of the probe to one or more nucleic acids in the sample at a first temperature, which first temperature is at or below the second Tm, and
detecting hybridization of the probe to one or more nucleic acids in the sample at a second temperature, which second temperature is at or below the first Tm, but above the second Tm.

5. The method of claim 1 wherein the probe is labelled.

6. The method of claim 5 wherein the label is a fluorescent or a radioactive label, or is a ligand to which a secondary probe may bind.

7. The method of claim 5 wherein the label generates a differential signal depending on whether the probe has hybridized to a target strand or not.

8. The method of claim 1 further comprising a step of:
preferentially amplifying the second allele of the target sequence.

9. The method of claim 8 wherein the method comprises, prior to step c), steps of:
b2) providing to the reaction mix a pair of oligonucleotide primers for nucleic acid amplification, the pair of oligonucleotide primers hybridizing to the nucleic acid at first and second sites flanking the oligonucleotide probe binding site; wherein the Tm of the primer: sample is higher than the Tm of the probe: second allele;

b3) maintaining the reaction mix at a temperature between the probe: first allele Tm and the probe: second allele Tm, such that the probe preferentially hybridizes to the first allele;

b4) carrying out a thermal cycling amplification on the reaction mix, the amplification including a melt phase, an annealing phase, and an extension phase, in which the temperatures of the extension and annealing phases are between the probe: first allele Tm and the probe: second allele Tm, such that the probe is hybridized to the first allele during these phases; to thereby amplify the second allele; and wherein step c) comprises detecting hybridization of the probe to the sample at a temperature at or below the probe: second allele Tm; detecting hybridization of the probe to the sample at a higher temperature at or below the probe: first allele Tm; and comparing the two; to thereby detect the amplified second allele.

10. The method of claim 9 wherein the step of detecting hybridized probe molecules further comprises quantification of relative amounts of first and second alleles in the reaction mix.

11. The method of claim 10 wherein the ratio of first to second alleles is quantified by: maintaining the reaction mix at a first temperature at or below the Tm of the probe: second allele; detecting hybridized probe molecules; increasing the reaction mix to a second temperature above the Tm of the probe: second allele but at or below the Tm of the probe: first allele; and detecting hybridized probe molecules.

12. The method of claim 9 wherein the pair of primers comprises a first primer that binds 3'-wards of the probe target, and a second primer that binds 5'-wards of the probe target.

13. The method of claim 9 wherein one of the primers is provided in a rate-limiting amount, and the amplification reaction is asymmetric PCR.

14. The method of claim 1 wherein the probe comprises a first nucleic acid sequence that is complementary to a first target nucleic acid sequence; a second nucleic acid sequence that is complementary to a second target nucleic acid sequence; and a linker nucleic acid sequence joining the first and second nucleic acid sequences; wherein the linker separates the two first and second sequences such that the melting temperatures of the first sequence annealed to the first target nucleic acid sequence and of the second sequence annealed to the second target nucleic acid sequence are discrete.

15. The method of claim 14 wherein both of the first and second nucleic acid sequences are reporter regions, each comprising a label.

16. The method of claim 1 wherein the probe comprises a blocking region.

17. The method of claim 1 wherein the target sequence is a portion of a microbial drug resistance gene.

* * * * *